United States Patent [19]

Tihon et al.

[11] 4,350,768

[45] Sep. 21, 1982

[54] METHOD FOR PREPARING SINGLE CELL SUSPENSION

[75] Inventors: Claude Tihon, Manlius; M. E. Curry, Syracuse, both of N.Y.

[73] Assignee: Bristol Myers Company, New York, N.Y.

[21] Appl. No.: 188,710

[22] Filed: Sep. 19, 1980

[51] Int. Cl.³ .................. C12N 5/02; B01D 29/00; B26B 27/00

[52] U.S. Cl. .................. 435/241; 435/803; 210/460; 210/927; 241/30; 241/169.2

[58] Field of Search ............. 435/240, 241, 284, 286, 435/803, 1, 261; 210/927, 416.1, 416.3; 241/95, 283, 30, 169, 169.2; 128/218 M, 220, 272

[56] References Cited

U.S. PATENT DOCUMENTS

| | | | |
|---|---|---|---|
| 850,357 | 3/1907 | Doyle | 128/234 |
| 853,796 | 6/1907 | Imes et al. | 83/437 |
| 1,000,641 | 1/1911 | Tebbit | 366/176 |
| 1,404,652 | 8/1922 | Rohnow | 48/180 R |
| 1,512,644 | 4/1924 | Smith | 83/437 |
| 2,437,818 | 3/1948 | Hetzler | 83/437 |
| 3,451,777 | 6/1969 | DiGiuio | 83/437 |
| 3,493,503 | 2/1970 | Mass | 210/778 |
| 3,802,843 | 4/1974 | Kim | 422/71 |
| 3,941,317 | 3/1976 | Kanor | 241/21 |
| 3,975,631 | 8/1976 | Bonfield | 250/211 R |

FOREIGN PATENT DOCUMENTS 1356794 6/1974 United Kingdom ............... 435/241

OTHER PUBLICATIONS

Park et al., J. Nat. Cancer Institute, vol. 46, No. 2, pp. 411-422 (1971).
Bergsagel et al., J. Nat. Cancer Institute, vol. 28, pp. 2187-2196 (1968).
Ogawa et al., J. Hematology, vol. 41, No. 1, pp. 7-15 (1973).
Steel et al., Cancer Research, vol. 35, pp. 1530-1535.
Fidler; Cancer Research, vol. 34, pp. 491-497 (1974).
Thomas Scientific Apparatus Catalog; p. 412 (1980).

*Primary Examiner*—Raymond N. Jones
*Assistant Examiner*—Elizabeth J. Curtin
*Attorney, Agent, or Firm*—Roylance, Abrams, Berdo & Farley

[57] ABSTRACT

A method and apparatus for preparing a liquid suspension of single, independent tissue cells for, e.g., subsequent cell proliferation as by in vitro culturing, is disclosed. The method involves introducing the combination of subdivided tissue and liquid medium into a chamber defined in part by a foraminous wall portion, and contracting the chamber to force the tissue through the foraminous wall, thereby further subdividing the tissue. An apparatus embodiment includes the combination of confining means for confining a liquid suspension of tissue; a screen; means supporting the screen; and pump means for passing the liquid suspension of tissue from the confining means back and forth through the screen.

20 Claims, 8 Drawing Figures

METHOD FOR PREPARING SINGLE CELL SUSPENSION

BACKGROUND OF THE INVENTION

1. Field of the Invention

The invention provides a method and apparatus for preparing a suspension of single cells. The invention is characterized by the step of subdividing an animal or vegetable tissue sample by hydraulically forcing the sample back and forth through a finely apertured wall.

2. Description of the Prior Art

Recent techniques for study of animal and plant tissues have involved the culturing of independent cells in vitro and the proliferation of animal cells in vivo as by injecting, for instance, tumor cells into a laboratory animal. In vitro culturing techniques are especially useful when it is desired to study human tumor cells or to biosynthesize a desired component of a tissue. Both in vitro culturing techniques and in vivo proliferation techniques require mincing of the tissue sample, which may be a solid tumor, and preparing a single cell suspension from the minced sample. Similarly, biological and biochemical tissue assay techniques often require the preparation of a single cell suspension from the tissue sample.

Prior art methods for preparing suspensions of single cells are often unduly time consuming and frequently damage the cells. Such methods involve both chemical, i.e., enzymatic, and physical techniques. Enzymatic techniques involve treating a coarsely subdivided tissue sample with a suitable enzyme, such as trypsin, capable of digesting the cell clusters or clumps sufficiently to break down the clusters or clumps into single independent cells. However, it is believed that enzymes adversely affect at least the surface of the cell and, therefore, such enzymatically-treated cells and their cultured progeny may have characteristics which are different from those of the original sample. If enzymatically-digested tumor cells are cultured in vitro and an effort is then made to study the response of the tumor cells to drugs, the response of the cultured cells and their progeny to drugs may be different from that which would be exhibited by the same tumor cells cultured without a history of enzymatic treatment.

Mechanical techniques for preparing single cell suspensions suffer similar drawbacks. One method involves forcing the minced animal tissue sample through successively smaller gauges of hypodermic needles, using a syringe. However, the amount of force necessary to push the minced tissue through the single extended aperture of the hypodermic needle requires that the tissue sample be exposed to hydrostatic pressures so high as to result in possible injury to the cells. Moreover, the procedure is unduly slow and requires excessive amounts of laboratory personnel time.

Another prior art procedure involves placing the minced tumor sample upon the surface of a fine wire mesh screen and forcing the sample through the screen with, e.g., a rubber plunger. The subdivided sample so produced is recovered and the operation is repeated several times with increasingly finer mesh screens until the tissue has been sufficiently subdivided. This procedure is extremely time consuming. Moreover, the bottom of the screen is often placed upon a solid surface for support while the material is forced through the screen so that the cells are pressurized between hard surfaces on both sides of the screen with likelihood of excessive cell trauma.

SUMMARY OF THE INVENTION

The method and apparatus of the invention are useful whenever it is desired to provide a single cell suspension from animal tissue or soft vegetable tissue. The invention is especially useful in preparing a single cell suspension for subsequent cell proliferation, either by culturing in vitro or in vivo proliferation. For example, the invention is useful in preparing a single cell suspension from a solid tumor sample or a liquid tumor sample derived from, e.g., ascites fluids, pleural effusion or the like, which liquid tumors comprise tumor cell clumps. The use of the method and apparatus of the invention is especially advantageous when it is desired to provide a single cell suspension from a solid tumor sample for subsequent in vitro culturing.

A coarsely subdivided tissue sample is converted into suspension of single independent cells according to the invention by combining the subdivided tissue sample with sufficient buffered, aqueous, liquid medium to encompass the subdivided sample; introducing the resulting combination into an expansible and contractible chamber defined in part by a finely-apertured wall portion; and forceably contracting the chamber to force the sample material through the foraminous wall portion, thereby further subdividing the sample. Advantageously, the step of introducing the combination of subdivided sample material and liquid medium into the expansible and contractible chamber is accomplished by positioning the foraminous wall portion adjacent the combination of sample and liquid and expanding the chamber to force the sample material into the chamber hydraulically. Expansion and contraction of the chamber is best repeated a plurality of times, thereby forcing the subdivided sample back and forth through the apertured wall portion. Following repeated expansion and contraction of the chamber, a foraminous wall portion having smaller apertures can be substituted for the first foraminous wall portion and the tissue further subdivided by hydraulically forcing the tissue back and forth through the second foraminous wall.

Apparatus embodiments of the invention comprises the combination of: confining means for confining a quantity of liquid having animal tissue dispersed therein; a screen; means supporting the screen; and pump means for passing the liquid and tissue combination from the confining means back and forth through the screen. Other apparatus embodiments of the invention provide piston-and-cylinder means defining an expansible and contractible chamber having an opening and a plurality of unitary, finely-apertured screens, each screen being detachably connectable to the cylinder to cover the opening and provide finely-apertured openings to the chamber. At least one of the unitary, finely-apertured screens has uniform apertures of a size in the range of between about 15–100$\mu$, advantageously about 400 U.S. mesh or about 36$\mu$.

Preparation of a single cell suspenion according to method and apparatus embodiments of the invention provides advantages over prior art methods and apparatus, including substantial savings in time and labor and less trauma to the cells during preparation.

IDENTIFICATION OF THE DRAWINGS

In the drawings which form part of the original disclosure of the invention:

DETAILED DESCRIPTION OF THE METHOD

Figure 1:
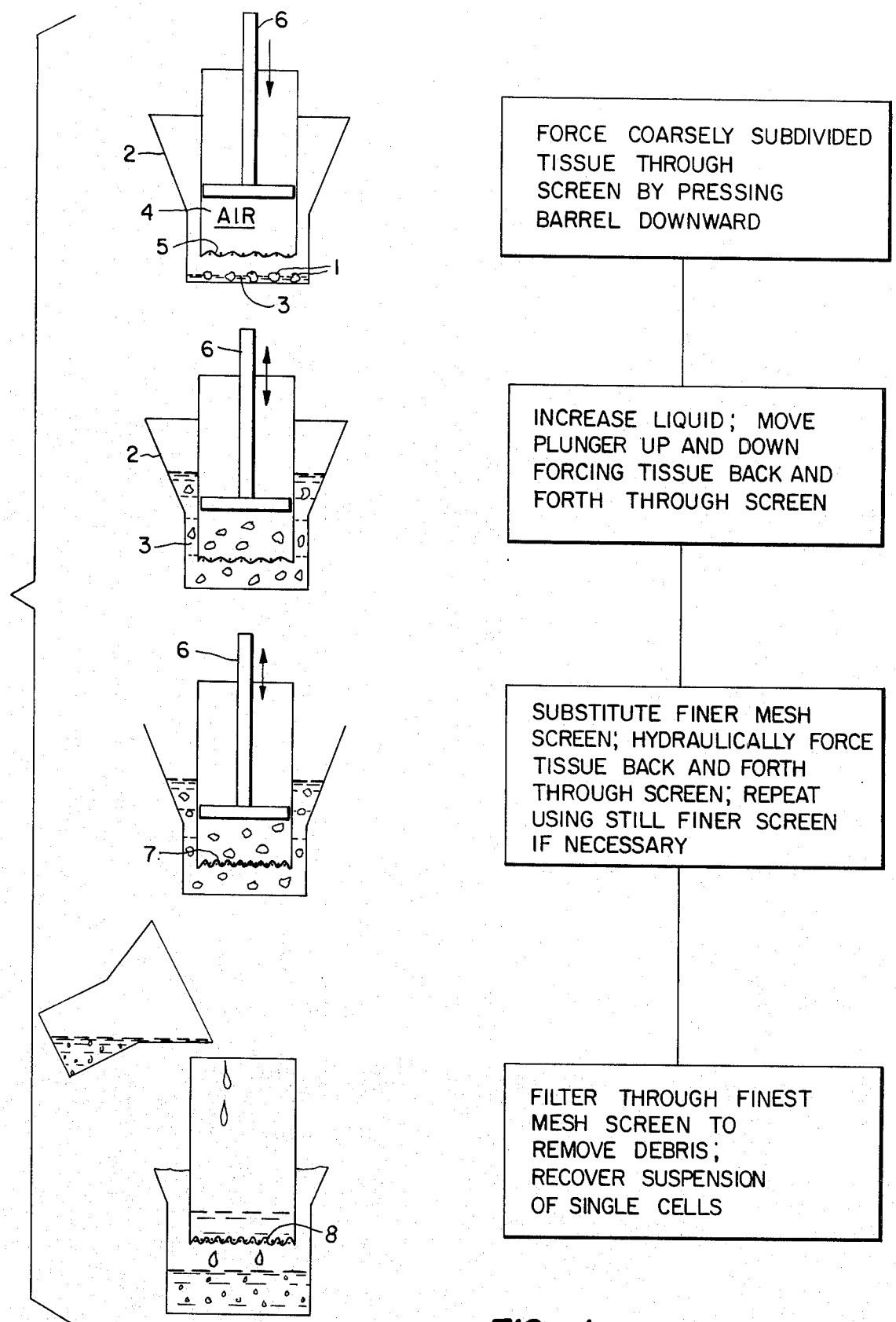
FIG. 1 is a flow sheet, including semi-diagramatic illustrations, of one method embodiment of the invention.

The invention is best understood with reference to the method and to FIG. 1, which illustrates an embodiment of the method. A coarsely subdivided tissue sample 1, such as finely chopped solid human tumor, is provided. Initial subdivision of the tissue is accomplished by any conventional means known to those skilled in the art, such as by using the "cross scalpel" method. Advantageously, four scalpels can be provided. Two of the scalpels can be bound together in side-by-side fashion so that the parallel blades are at a distance of 1 to 3 millimeters. The second set of scalpels are bound together in the same fashion, and the two sets of instruments used in "cross-scalpel" fashion as by cutting the sample simultaneously with both instruments with the direction of movement of the instruments being opposite to each other. A sample subdivided in this manner will comprise substantially cubical pieces having dimensions on the order of 1 to 3 mm.

The subdivided tissue is placed into a suitable container 2 and wetted with a buffered aqueous liquid medium 3, which is advantageously the same liquid medium which is to be thereafter utilized in assaying or proliferating the cells. An expansible and contractible chamber 4 having an opening covered by a foraminous wall portion 5, such as a screen, is provided. The expansible and contractible chamber illustrated comprises a piston and cylinder means, such as a conventional syringe barrel and plunger, with the end of the syringe having been removed and replaced by a screen. Additionally, the end of the conventional plunger is advantageously modified to provide a flat end for better contact between the screen and the end of the plunger. The expansible chamber 4 has been expanded by means of plunger 6 to provide an empty, i.e., air-filled, chamber. Thereupon, the screen is forced downwards upon the tissue sample by pressing down the modified syringe barrel to force the tissue upwardly through the screen, thus further subdividing the tissue. The operation is repeated until substantially all of the tissue has been forced through the screen and into the chamber.

Thereupon, more liquid 3 is added to the sample either through the chamber after removal of the plunger 6 or directly to the container 2. Sufficient liquid should be added to encompass all of the tissue within the liquid phase. Advantageously, sufficient liquid is added to provide a substantial excess of liquid by volume over the volume of the subdivided sample. The chamber is forceably contracted and expanded by moving the plunger 6 up and down while holding screen 5 near the bottom of container 2, and the tissue is thus caused to flow back and forth through the screen and is thereby further subdivided. The operation is continued until all of the tissue pieces are of substantially the same size and the mixture is homogenous. For a solid tumor sample weighing about 1 gram, a 20 U.S. mesh screen has been found to be suitable for the first operation. A tissue-liquid volume of about 30 to about 50 milliliters has also been found to be suitable. Under these conditions, it has been found that expansion and contraction of the chamber about 20 times will provide substantially uniform sized subdivided tissue pieces.

Upon completion of the first operation, a finer mesh screen is provided and substituted for the previously-used screen. This can be accomplished by providing a chamber, e.g., a syringe barrel, comprising means for receiving different sized screens or by the substitution of a second modified syringe barrel having a finer mesh screen permanently attached thereto. The suspension of previously-subdivided animal tissue is hydraulically-forced back and forth through the screen by forceably moving plunger 6 up and down a plurality of times until the subdivided tissue is of uniform size. Thereafter, the operation is repeated using a still finer mesh screen 7. A recommended series of increasingly finer mesh screens is: 20, 60, 100, 200 and 400 U.S. mesh. However, a fewer or greater number of screens can be used depending on the ease or difficulty of subdividing the particular animal tissue. The final screen used will be one having apertures of a size in the range of between about 15 to $100\mu$, advantageously between about 20 to $70\mu$, more advantageously between about 20 and $50\mu$. A 400 U.S. mesh screen has apertures of about $38\mu$ and is especially advantageous.

Once the suspension has been repeatedly forced back and forth through a screen having apertures in the above range, e.g., a 400 mesh screen, the resultant liquid suspension will comprise single animal cells. While tissue cells have a size in the range of between about 6 to $15\mu$, as indicated above, the finest apertures used in this invention need not be so small since the generation of single cells is partially the result of shearing force caused by repeated passage of the cell clumps back and forth through the apertured wall.

Thereupon, it is advantageous to filter the suspension through the finest mesh screen 8 using only gravity to effect the filtration. Debris is then retained on the screen and the filtrate will comprise the suspension of single, individually suspended cells suitable for proliferation as by in vitro culturing.

Figure 2:
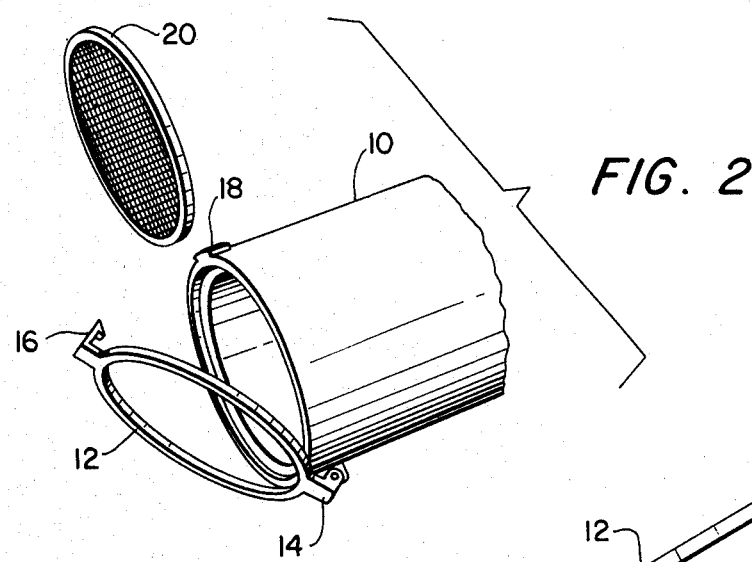
FIG. 2 is a fragmentary perpsective view illustrating one means for detachably securing a screen according to the invention.
Figure 2A:
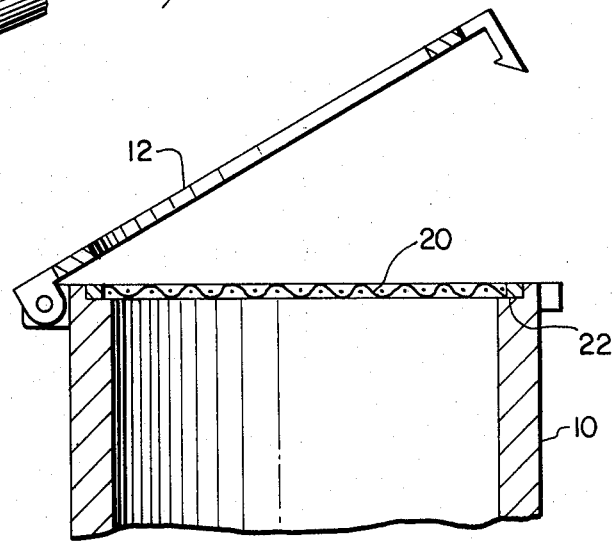
FIGS. 2a and 2b are fragmentary sectional views showing parts of the structure of FIG. 2 in different relative positions.
Figure 2B:
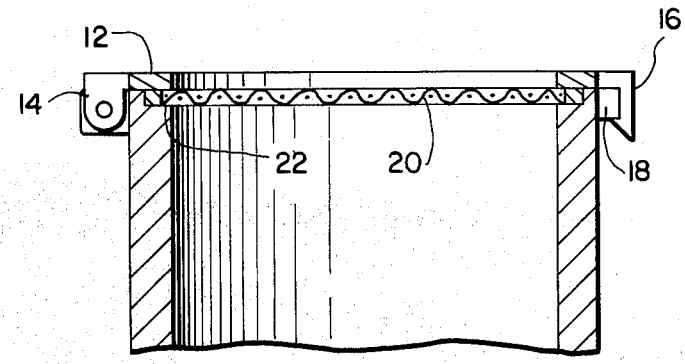

The Apparatus of FIGS. 2, 2a and 2b

The invention additionally provides apparatus for conducting the method of the invention. In one embodiment, the apparatus comprises the combination of piston and cylinder means defining an expansible and contractible chamber having an opening and a plurality of unitary, foraminous screen means detachably connectable to the piston and cylinder means to cover the opening. At least one of the unitary, foraminous screen means comprises apertures of a size in the range of between about 15 and $100\mu$, advantageously between about 20 and $70\mu$, more advantageously between about 20 and $50\mu$, most advantageously about $38\mu$ or 400 mesh.

Fragmentary views of a portion of such apparatus are shown in FIGS. 2, 2a and 2b. The apparatus includes a cylinder 10, such as a syringe barrel, and an annular retaining element 12 attached at its periphery by a hinge 14 to the open end of cylinder 10. Element 12 is shown in FIG. 2a in an open position and in FIG. 2b in a closed position wherein element 12 is latched by means of elements 16 of the annular retaining means and 18 of the cylinder. In the closed position, screen means 20 is held between the annular retaining element and the open end of the cylinder, which includes an inset shoulder portion 22 upon which the screen rests. Not shown are the piston means designed to cooperate with cylinder 10 to form an expansible and contractible chamber in the interior and of cylinder 10, as in FIG. 1. Additionally not shown are the additional unitary finely-apertured screens which, together, provide increasingly smaller apertures.

Figure 6:
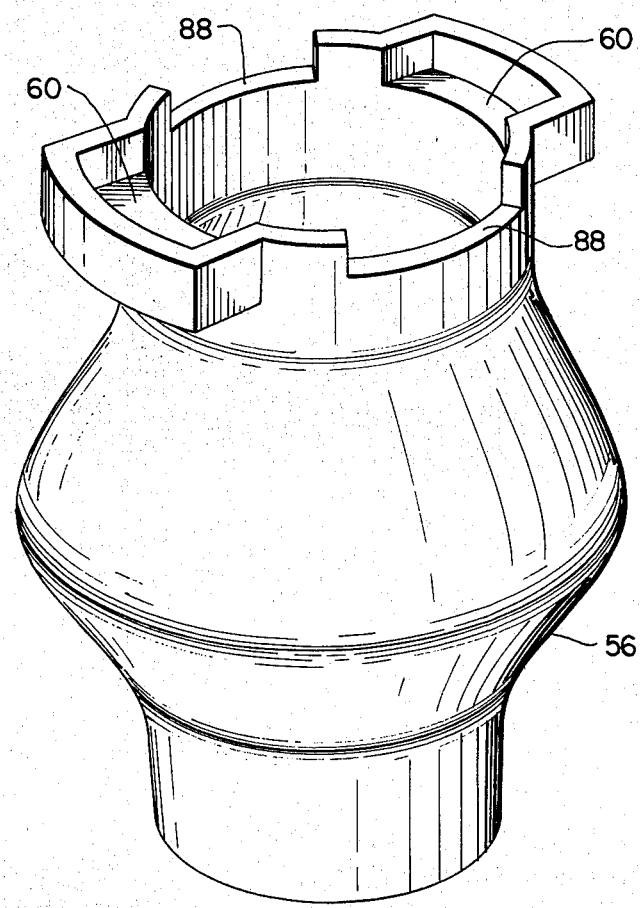
FIG. 6 is a perspective view of a portion of the apparatus of FIG. 4.

Use of such apparatus may be conducted with a conventional container means; however, advantageously a container such as that illustrated in FIGS. 1 and 6 can be used, wherein the internal transverse dimension of the container adjacent the bottom wall is larger than the external transverse dimension of the cylinder by an amount such that the annular side wall of the container closely surround the cylinder when the cylinder is disposed in the container with its opening closely adjacent the bottom wall of the container. Use of such a container more readily subjects the tissue/liquid mixture to hydraulic force without manipulation of the container.

Figure 3:
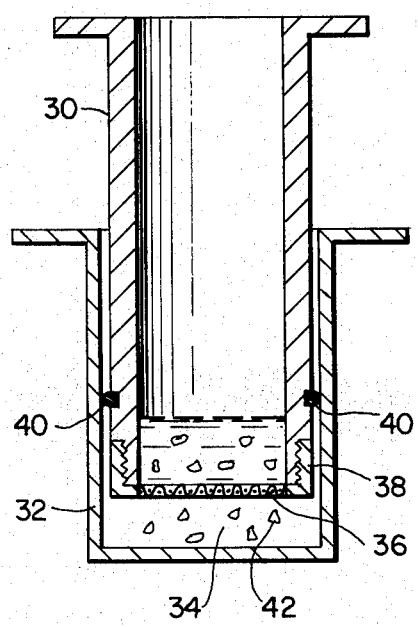
FIG. 3 is a vertical sectional view of another apparatus embodiment of the invention.

The Apparatus of FIG. 3

In another aspect of the invention, an apparatus for conducting the method of the invention is provided which comprises a combination of confining means for confining a quantity of liquid cell suspension; a screen; means supporting the screen; and pump means for passing a liquid suspension of animal or plant tissue from the confining means back and forth through the screen. An embodiment of such apparatus is shown in FIG. 3, wherein the pump means and container means, together, comprise two telescopically-related members, female member 32 and male member 30, which define an expansible and contractible chamber 34 having an open end. The screen means 36 is shown to be detachably secured across the open end of the chamber by means of threaded retainer 38 supported upon the end of male member 30. Relative movement of the two telescopically-related members in one direction will cause the chamber 34 to expand, whereas relative movement in the other direction will cause the chamber to contract. Thus, movement of male member 30 in an upward direction will cause chamber 34 to expand, while movement of male member in a downward direction will cause chamber 34 to contract. A sealing means, such as O ring 40, is retained on the outer surface of male member 30 to provide a seal for chamber 34. The screen means is shown to be in contact with a liquid suspension of animal tissue, whereby relative movement of the telescopically-related members to expand the chambers will cause the suspended animal tissue to flow through the screen in one direction and relative movement of the telescopically-related members in an opposite direction will cause the animal tissue to flow through the screen in the opposite direction.

Thus, the male member 30 can be caused to reciprocate upwardly and downwardly causing the liquid suspension of animal tissue 42 to be pumped back and forth through the screen means, thereby subdividing the animal tissue. The screen means 36 is replaced with a screen means having smaller apertures and the operation repeated. Finally, when a screen means 36 having apertures of a size in the range of between 15 to 100μ, advantageously 20 to 70, most advantageously 20 to 50μ is used, the resultant suspension will comprise single animal cells.

Figure 4:
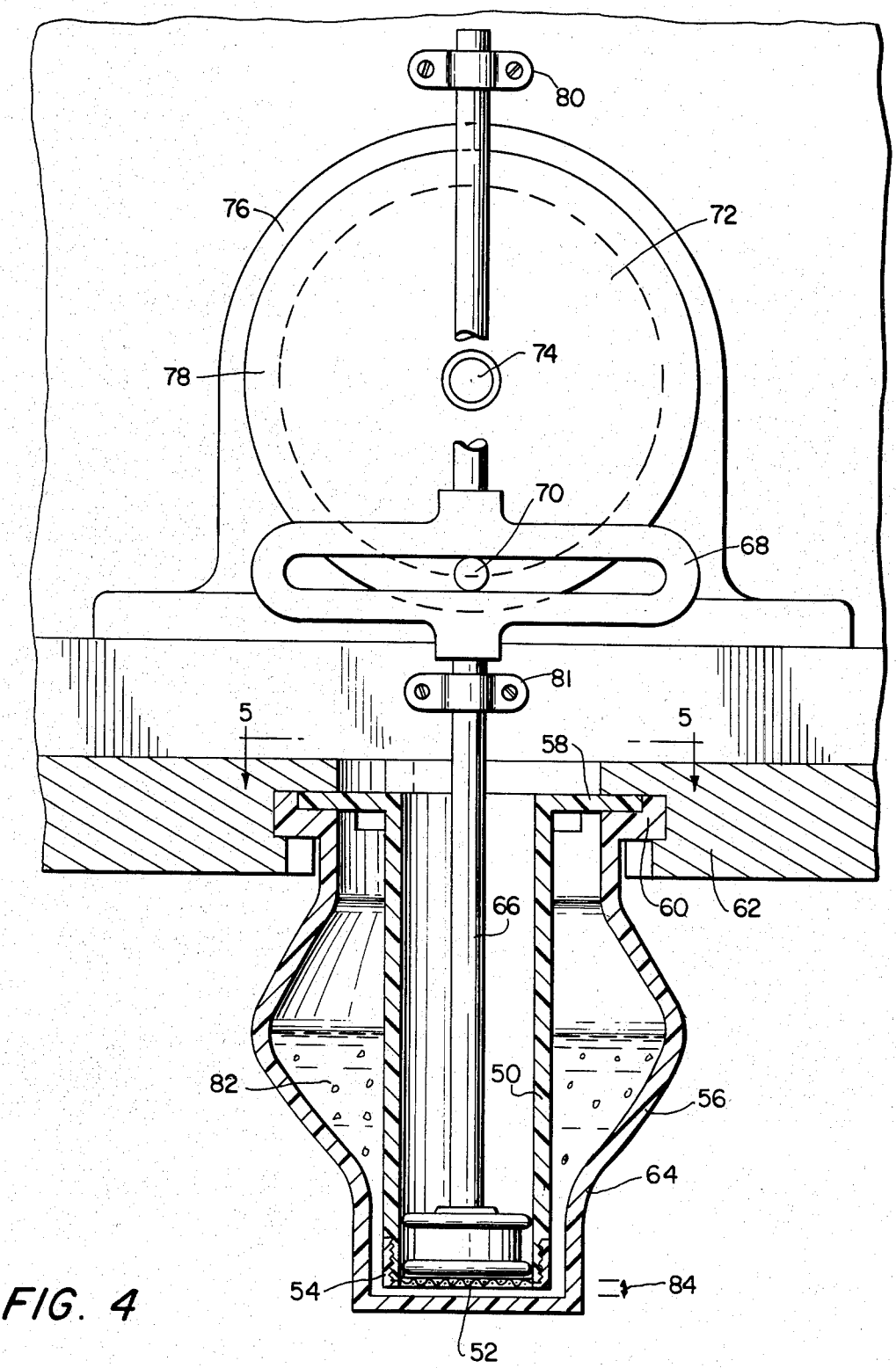
FIG. 4 is a vertical sectional view of a further apparatus embodiment of the invention with parts thereof shown in elevation.
Figure 5:
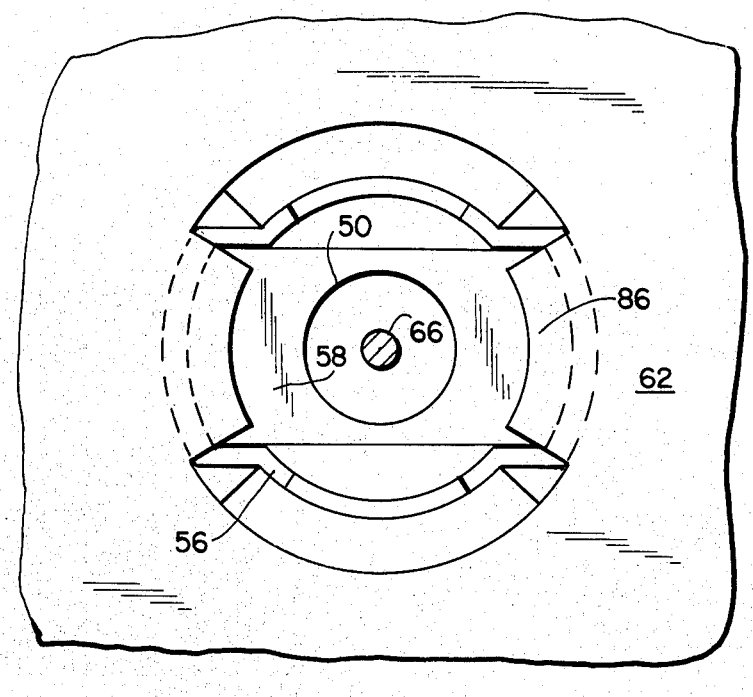
FIG. 5 is a horizontal sectional view taken generally on line 5—5, FIG. 4.

The Apparatus of FIGS. 4–6

In this apparatus embodiment three telescopically-related members, two defining an expansible and contractible chamber and the third defining a confining means, are provided. The apparatus comprises a tubular cylinder 50 having an open end covered by screen 52 which is detachably secured to the open end by threads 54. Cylinder 50 extends downwardly into a container 56 and is secured by means of an external ear 58 of the cylinder between shoulder 60 of the container and support means 62. A piston or plunger 64 constitutes the third telescopic member and can be caused to reciprocate upwardly and downwardly by drive means, including shaft 66 connected to slotted yoke 68 which in turn engages a pin 70 fixed to and projecting from a solid plate 72. The plate is secured to and driven by output shaft 74 of an electric, constant speed, gear reduction motor 76. Rotation of the plate 72 causes pin 70 to rotate along the circular path 78, causing shaft 66, which is restrained by vertically-aligned bearings 80 and 81, to move up and down. Such reciprocating motion of the plunger causes the suspension of animal tissue 82 held by container 56 to flow back and forth through screen 52 which is located at a distance from about 1 to about 3 mm from the bottom wall of container 56 as shown at 84.

At the bottom of container 56, the side wall of the container is right cylindrical and closely surrounds the lower end of cylinder 50, the small volume of the annular space between the cylindrical side wall and the cylinder assuring that substantially all of the liquid suspension in the annular space will be induced to flow through the screen. In a location spaced well above the lower end of cylinder 50, the side wall of the container is enlarged to provide a reservoir. As shown, the side wall has an annular outwardly bulged portion so as to present a generally convex outer surface and a generally concave inner surface, tapering from the largest diameter near the midpoint downwardly and inwardly to join the lower, right cylindrical side wall portion. The larger upper end of the side wall of the container provides for easier mounting of the container and the cylinder on support 60. The enlarged reservoir portion of the container assures that the total annular space between the cylinder and the container side wall will provide a reservoir of adequate volume to accommodate the volume of liquid which can be handled by the cylinder. If desired, the side wall portion of the container above the bottom, right cylindrical side wall portion may be of a simple frustroconical construction such as is illustrated in FIG. 1.

Support 62 includes an ear 86, FIG. 5, for detachably securing cylinder 50 to the support by engaging ear 58 of the cylinder between ear 86 of the support and recessed shoulder 60, FIG. 6, of the container. Notches 88 are provided in the upper edge of the side wall of container 56, between shoulder 60, to allow the cylinder 50 to be pressed onto the bottom wall of the container when desired, the notches accommodating ears 58 when the cylinder has been rotated to the proper position relative to the container. It will be apparent that the apparatus of FIGS. 4–6 can be operated to accomplish the successive cycles of pumping the liquid cell suspension through the screen in a controlled fashion which reduces the possible effects of varying capabilities of operating personnel. Thus, motor 76 can be controlled by a conventional timer (not shown) with the timer being set to provide a predetermined number of reciprocations of shaft 66 and plunger 64. Similarly, the speed reducer of gear motor 76 can be adjustable, increasing the amounts of control available.

EXAMPLE 1

An ovarian solid tumor sample measuring about ½ cm by 1 cm by ¼ cm and weighing about 1 gram was precut with cross scalpels into cubes having dimensions of about 1 to 3 mm, and the cubes were placed in a 100 ml petri dish. McCoy's 5A Growth Medium was added to the minced sample in an amount (about 2 ml) sufficient to wet all of the sample.

A polyethylene syringe barrel was modified by cutting off the lower (needle) end to provide an open ended syringe barrel which was then permanently covered with a circular piece of 20 U.S. mesh screen by fusing the polyethylene barrel to the periphery of the screen. The screen covered end of the syringe barrel was forced down on the minced sample, thereby forcing the sample upwardly through the screen and into the barrel. This procedure was repeated with the portions of the sample remaining in the petri dish until substantially all the minced sample had been forced through the screen and into the open barrel (about 10–15 repititions).

Thereupon, the modified syringe body containing the thus further subdivided tumor was transferred to a 150 ml beaker and a sufficient amount of McCoy's 5A Growth Medium was added to bring the total volume of the tumor and liquid sample to 40 ml.

The syringe plunger (modified slightly by cutting the rubber end to provide a flat end surface) was then inserted into the modified syringe barrel, and the syringe body was positioned so that the screen was just above the bottom of the beaker. The plunger was then rapidly moved in an up and down motion, thus forcing the minced sample to flow back and forth through the screen until all the material flowed readily through the screen (about 20 repititions). The plunger was then forced to the fully closed position, thereby removing all material from the syringe barrel, and the syringe was then removed from the beaker.

A syringe body was modified as before; however, the open end of the cylinder was covered with a 60 U.S. mesh screen. The procedure described in the paragraph immediately above was repeated.

Syringe bodies, modified as before but with coverings of 100, 200 and 400 U.S. mesh screens, respectively, were provided. The above procedure was repeated with each syringe body using the 100 mesh covered body, then the 200 mesh covered body and finally the 400 mesh covered body.

The plunger was removed from the 400 mesh covered syringe barrel and the tumor suspension poured through the barrel and thus through the 400 mesh screen into a clean 150 ml beaker, without the use of the plunger. Debris was retained on the screen. The tumor cell suspension in the fresh 150 ml beaker was suitable for a human tumor cloning assay.

Although the invention has been described in detail with particular reference to specific advantageous embodiments thereof, modifications and variations can be made without departing from the scope and spirit of the invention as described in the specification and defined in the appended claims.

What is claimed is:

1. The method for preparing a suspension of single tissue cells comprising the steps of:
   providing a subdivided tissue sample;
   combining the subdivided sample material with sufficient buffered aqueous liquid medium to encompass the sample;
   introducing the resulting combination into an expansible; and contractible chamber defined in part by a finely-apertured foraminous wall portion;
   providing a container to receive the resulting combination; and
   forcibly contracting the chamber to force the sample material through the foraminous wall portion into said container, thereby further subdividing the sample material.

2. The method according to claim 1, wherein:
   the steps of introducing the sample material into the chamber and then contracting the chamber to force the sample material through the foraminous wall portion are repeated a plurality of times.

3. The method according to claim 2, wherein:
   the step of introducing the combination of subdivided sample material and liquid medium into the chamber is accomplished by positioning the foraminous wall portion adjacent the sample material and expanding the chamber to force the sample material into the chamber via the apertures of the foraminous wall portion.

4. The method according to claim 3, wherein:
   the volume of liquid medium combined with the subdivided sample material is substantially in excess of the volume of the subdivided sample material;
   the combination of liquid medium and sample material is initially disposed in said container; and
   the foraminous wall portion is immersed in the liquid medium.

5. The method according to claim 3, wherein after the expansion and contraction steps have been repeated a plurality of times, said steps are again repeated a plurality of times using at least one foraminous wall portion having smaller apertures.

6. The method according to claim 5, wherein:
   the volume of liquid combined with the subdivided sample material is substantially in excess of the volume of subdivided sample material;
   the combination of liquid medium and sample material is disposed in a container and the foraminous wall portion is immersed in the container; and
   the expansible and contractible chamber being defined in part by a piston and cylinder such that the outer transverse dimension of the cylinder is smaller than the inner transverse dimension of the container near its bottom by an amount such that the side walls of the container closely surround the cylinder when the cylinder is disposed in the container with the foraminous wall covered opening of the cylinder adjacent the bottom of the container.

7. The method according to claim 5, wherein the tissue is an animal tissue.

8. The method according to claim 7, wherein the animal tissue is from a human tumor.

9. The method according to claim 8, wherein the final repetitions of expansion and contraction of the chamber are conducted using a foraminous wall portion having apertures of a size in the range of from about 20 to 70μ.

10. The method according to claim 9, wherein at least three foraminous wall portions having increasingly small apertures are used.

11. The method for preparing a suspension of single tissue cells comprising the steps of:
providing a subdivided tissue sample;
placing the subdivided sample material into a suitable container with sufficient buffered aqueous liquid medium to encompass the sample;
introducing into said container and partly below the surface of said medium an expansible and contractible chamber defined in part by a foraminous finely-apertured lower wall portion; and forcibly contracting the chamber to force the sample material through said foraminous wall portion, thereby further subdividing the sample material.

12. The method according to claim 11, wherein the steps of introducing the sample material into the chamber and then contracting the chamber to force the sample material through the foraminous wall portion are repeated a plurality of times.

13. The method according to claim 12, wherein the step of introducing the combination of subdivided sample material and liquid medium into the chamber is accomplished by positioning the foraminous wall portion adjacent the sample material and expanding the chamber to force the sample material into the chamber via the apertures of the foraminous wall portion.

14. The method according to claim 13, wherein the volume of liquid medium combined with the subdivided sample material is substantially in excess of the volume of the subdivided sample material.

15. The method according to claim 12, wherein after the expansion and contraction steps have been repeated a plurality of times, said steps are again repeated a plurality of times using at least one foraminous wall portion having smaller apertures.

16. The method according to claim 15, wherein:
the volume of liquid combined with the subdivided sample material is substantially in excess of the volume of subdivided sample material; and
the expansible and contractible chamber are defined in part by a piston and cylinder such that the outer transverse dimension of the cylinder is smaller than the inner transverse dimension of the container near its bottom by an amount such that the side walls of the container closely surround the cylinder when the cylinder is disposed in the container with the foraminous wall covered opening of the cylinder adjacent the bottom of the container.

17. The method according to claim 15, wherein the tissue is an animal tissue.

18. The method according to claim 17, wherein the animal tissue is from a human tumor.

19. The method according to claim 18, wherein the final repetitions of expansion and contraction of the chamber are conducted using a foraminous wall portion having apertures of a size in the range of from about 20 to 70μ.

20. The method according to claim 19, wherein at least three foraminous wall portions having increasingly small apertures are used.

* * * * *